United States Patent [19]

Iwasaki et al.

[11] Patent Number: 4,940,582
[45] Date of Patent: Jul. 10, 1990

[54] ANTIBIOTIC YI-HU3

[75] Inventors: Tetsuji Iwasaki; Toshio Uesaka, both of Wakayama, Japan

[73] Assignee: Kao Corporation, Tokyo, Japan

[21] Appl. No.: 243,033

[22] PCT Filed: Dec. 21, 1987

[86] PCT No.: PCT/JP87/01007
§ 371 Date: Aug. 15, 1988
§ 102(e) Date: Aug. 15, 1988

[87] PCT Pub. No.: WO88/04661
PCT Pub. Date: Jun. 30, 1988

[30] Foreign Application Priority Data

Dec. 23, 1986 [JP] Japan ................................. 61-307164

[51] Int. Cl.$^5$ .................... A61K 35/74; C12R 1/38; C07G 11/00; C12P 1/04
[52] U.S. Cl. .................. 424/115; 435/253.3; 435/874
[58] Field of Search ..................... 424/115; 435/253.3, 435/874

[56] References Cited

U.S. PATENT DOCUMENTS 4,062,943 12/1977 Lindberg ............................. 424/115

Primary Examiner—Herbert J. Lilling
Attorney, Agent, or Firm—Oblon, Spivak, McClelland, Maier & Neustadt

[57] ABSTRACT

The invention relates to antibiotic YI-HU3 and a process for preparing the same, which is produced by culturing a microorganism belonging to the genus of Pseudomonas, and which has antimicrobial and antitumor activities, and the following physicochemical characteristics:

(a) Molecular weight
   469
(b) Melting point
   180°–190° C.
(c) Ultraviolet absorption spectrum (in chloroform)

The maximum absorption is found in the neighborhood of 312 nm, with the second largest absorption being in the neighborhood of 300 nm.

(d) Infrared absorption spectrum (KBr Method)
   FIG. 2
(e) $^1$H—NMR spectrum (CDCl$_3$/CD$_3$OH)
   FIG. 3
(f) $^{13}$H—NMR spectrum (CDCl$_3$/CD$_3$OH)
   FIG. 4
(g) Solubility to solvents Soluble in methanol and chloroform, and not soluble in n-hexane.

(h) Color and state of the substance
   Light yellow crystals.

1 Claim, 4 Drawing Sheets

ANTIBIOTIC YI-HU3

FIELD OF THE INVENTION

This invention relates to a novel antibiotic. More particularly, the invention relates to novel antibiotic YI-HU3 possessing antimicrobial activity and antitumour activity as well as the process for preparing the same.

TECHNOLOGICAL BACKGROUND

Conventionally, various physiologically active substances which are produced by microorganisms are known in the art. Some of them are used as medicines.

There still exists, however, a desire for the development of -physiologically active substances which are more useful as medicines or agrochemicals.

DISCLOSURE OF THE INVENTION

The present inventors have isolated a number of microorganisms from natural soils and undertaken extensive studies on the product produced by such microorganisms. As a result, the inventors discovered that a strain separated from a soil at Wakayama Prefecture, Japan is capable of producing novel antibiotic YI-HU3 having antimicrobial and antitumour activities. The discovery has led to the completion of this invention.

Accordingly, an object of this invention is to provide novel antibiotic YI-HU3 and the process for preparing the same.

THE BEST MODE FOR PRACTICING THE INVENTION

Figure 1:
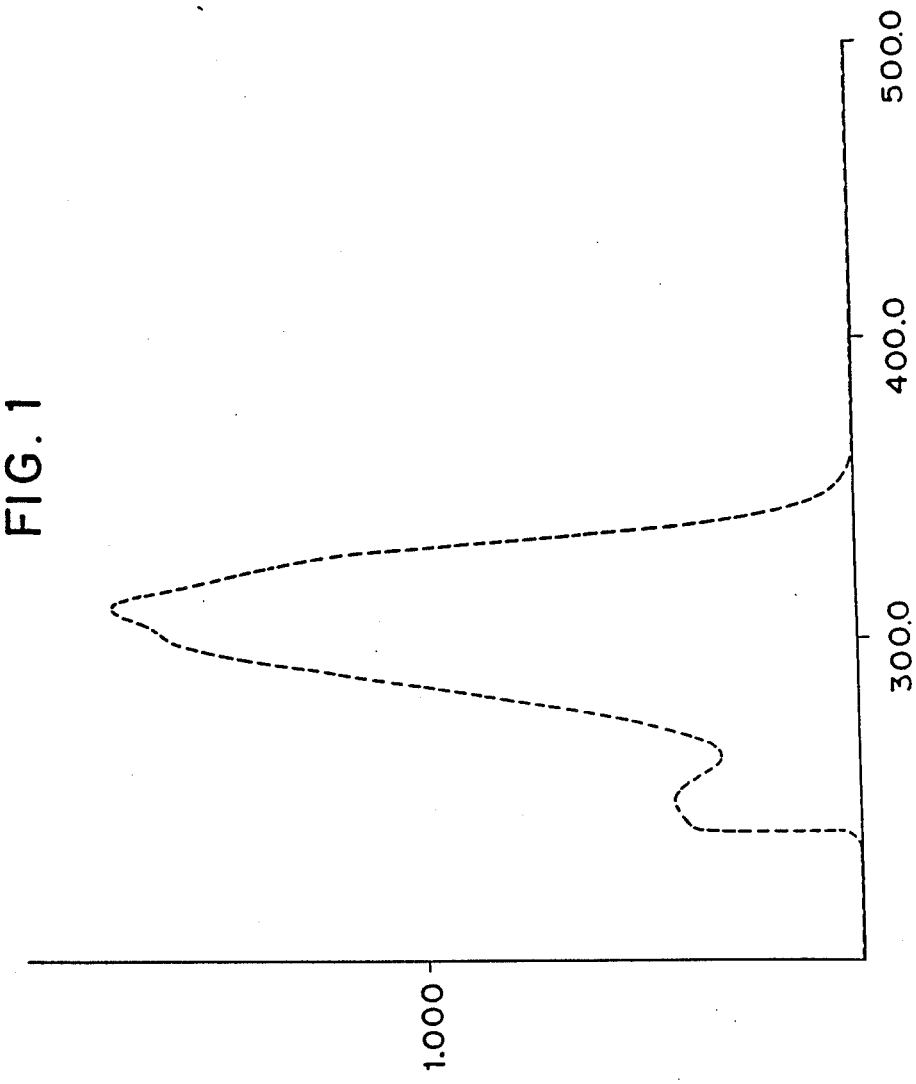
FIG. 1 shows the ultraviolet absorption spectrum of antibiotic YI-HU3 of this invention.

The strain YI-HU which is a typical microorganism producing the antibiotic YI-HU3 of this invention has the following characteristics:

(1) Morphology

Following characteristics were confirmed by the light or electron microscope observations of the microorganism of the YI-HU strain cultured in a potato-dextrose slant culture medium at 28° C. for 3 days.

The cells had a size of 1–5μ with no polymorphism. They had flagella and were mobile. No sporogenesis was observed. The Gram staining was negative and the strain had no acid fastness.

(2) Growth characteristics on various culture media:

The growth characteristics of the YI-HU strain on various culture media, as observed on the microorganisms cultured at 28° C. for 3 days, are as follows:

ar plate culturing (i) Meat extract agar plate culturing

The colony had a glossy, elevated disk-like shape with vitellus color. Color diffusion into the medium was not observed.

(ii) Meat extract liquid culturing

The medium turned wholly turbid and the bacteria grew light yellow, with a thin film being formed.

(iii) Meat extract gelatin stab culturing

The broth turned liquid with a film on its surface.

(3) Physiological Characteristics (i) General characteristics

| | |
|---|---|
| Nitrate reduction | negative |
| Indole production | negative |
| Starch hydrolysis | negative |
| Citric acid utilization | positive |
| Colored substance formation | positive |
| Urease | negative |
| Oxidase | positive |
| Reaction to oxygen | aerobic |
| Esculin hydrolysis | negative |
| Lysine decarbonation reaction | positive |
| Arginine decomposition | negative |
| Ornithine decarbonation reaction | negative |
| Acylamylase | negative |

(ii) Growth temperature range, when cultured in a potato-dextrose culture medium for 24 hours.

| Temperature (°C.) | Growth |
|---|---|
| 4 | − |
| 25 | + |
| 30 | + |
| 40 | + |
| 45 | − |

(iii) Anaerobic sugar decomposition (based on Hugh Leifson method at 30° C. for 7 days)

| Sugar | Conditions | Growth |
|---|---|---|
| Glucose | closed | − |
| | open | + |

(iv) Carbon source assimilation (at 30° C. for 7 days)

| Sugar | Growth |
|---|---|
| Xylose | + |
| Glucose | + |
| Fructose | + |
| Galactose | + |
| Maltose | − |
| Sucrose | − |
| Lactose | − |
| Mannitol | + |
| Starch | + |

(v) Fluorescent test under ultraviolet light
Negative (vi) Accumulation of polyhydroxybutylate (PHB)
Positive (vii) Presence of arginine dehydrolase
Negative Based on the above mycological characteristics, especially based on the fact that the microorganism (i) is a Gram-negative rod, (ii) is oxidase positive, (iii) has flagella and is mobile, (iv) is aerobic, and (v) is not sporogenous, the YI-HU strain is judged to be a strain belonging to Pseudomonas.

Further, according to the retrieval from *Bergey's Manual of Determinative Bacteriology* (8th edition) based on the above characteristics, *Pseudomonas gladioli* and *Pseudomonas cepacia* are detected as relatives of the YI-HU strain. *Pseudomonas cepacia*, however, is different from YI-HU in that the former assimilates sucrose and reduces nitrate into nitrite. On the other hand, *Pseudomonas gladioli* is different from YI-HU in that it assimilates sucrose positively.

Since the YI-HU strain is not identical with any of the known strain of microorganisms as discussed above, the inventors named this strain as *Pseudomonas sp. YI-HU* in order to distinguish it from other known microorganisms, and deposited it with Fermentation Research Institute, Agency of Industrial Science and Technology (1-1-3, Higashi, Tsukuba-shi, Ibaraki-ken, Japan), as FERM p-9035 on Nov. 8, 1987. On Dec. 10, 1987, the deposition was transferred to International Deposition as FERM BP-1610.

The antibiotic YI-HU3 of this invention may be prepared by seeding the above strain of microorganism in a culture medium containing nutrients, culturing it in an aerobic conditions, and collecting it from the culture broth. Any strains of microorganisms may be employed for producing the antibiotic YI-HU3 of this invention, inclusive of the above-mentioned YI-HU strain and its artificial or natural variants, so long as the same is capable of producing the antibiotic YI-HU3.

Culturing of the microorganisms producing the antibiotic YI-HU3 may be carried out in the following manner.

The microorganisms belonging to the strain of Pseudomonas which produces the antibiotic YI-HU3 of this invention may be cultured according to the same procedures as applied for culturing common Pseudomonas bacteria.

When the YI-HU strain is used, a preferable nutrient culture medium is a potato-dextrose medium containing potato extract and glucose.

Any culture methods conventionally employed for the production of antibiotics may be employed for culturing the microorganism of the YI-HU strain, although the liquid phase culture method is particularly suitable. Culturing is carried out in aerobic conditions, and at a temperature of 10° to 40° C. Generally, a preferable culturing temperature is in the neighborhood of 28° C. The production of the antibiotic YI-HU3 reaches the maximum in 2 to 5 days after commencing the culturing. When the amount of the antibiotic YI-HU3 accumulated in the culture broth reaches the maximum, culturing is terminated and the target substance is separated from the broth and refined.

The separation and purification of the antibiotic YI-HU3 may be performed by the application of various methods, either solely or appropriately combining two or more of them, taking into consideration the physicochemical characteristics of the substances as hereinafter discussed. More specifically, as the substance is usually contained in the culture broth and bacteria, the cultured mycelia is first separated by filtration, and then from the mycelia and the culture filtrate the antibiotic YI-HU3 is separated and purified by using one or more of the conventional means such as, for example, solvent extraction, a method using ion-exchange resins, gel filtration, absorption or partition column chromatography, dialysis, and precipitation.

One of the preferable methods of separating and purifying the antibiotic YI-HU3 may be illustrated as follows: The culture broth is separated by centrifugation into broth supernatant and mycelia. The broth supernatant is extracted by a water insoluble solvent such as chloroform. The extract is condensed and the residue is submitted to silica gel column chromatography. After the column was eluted by a suitable eluent such as chloroform, the active fractions are collected and concentrated. The residue obtained is dissolved into a suitable solvent such as a mixed chloroform-methanol solvent. Through addition of n-hexane to the solution, needle-like, light yellow crystals of the antibiotic YI-HU3 are obtained.

The antibiotic YI-HU3 obtained as above possesses the following physicochemical properties:

(a) Molecular weight
469

(b) Melting point
180°-190° C.

(c) Ultraviolet absorption spectrum (in chloroform)

The maximum absorption is found in the neighborhood of 312 nm, with the second largest absorption being in the neighborhood of 300 nm. (See FIG. 1)

Figure 2:
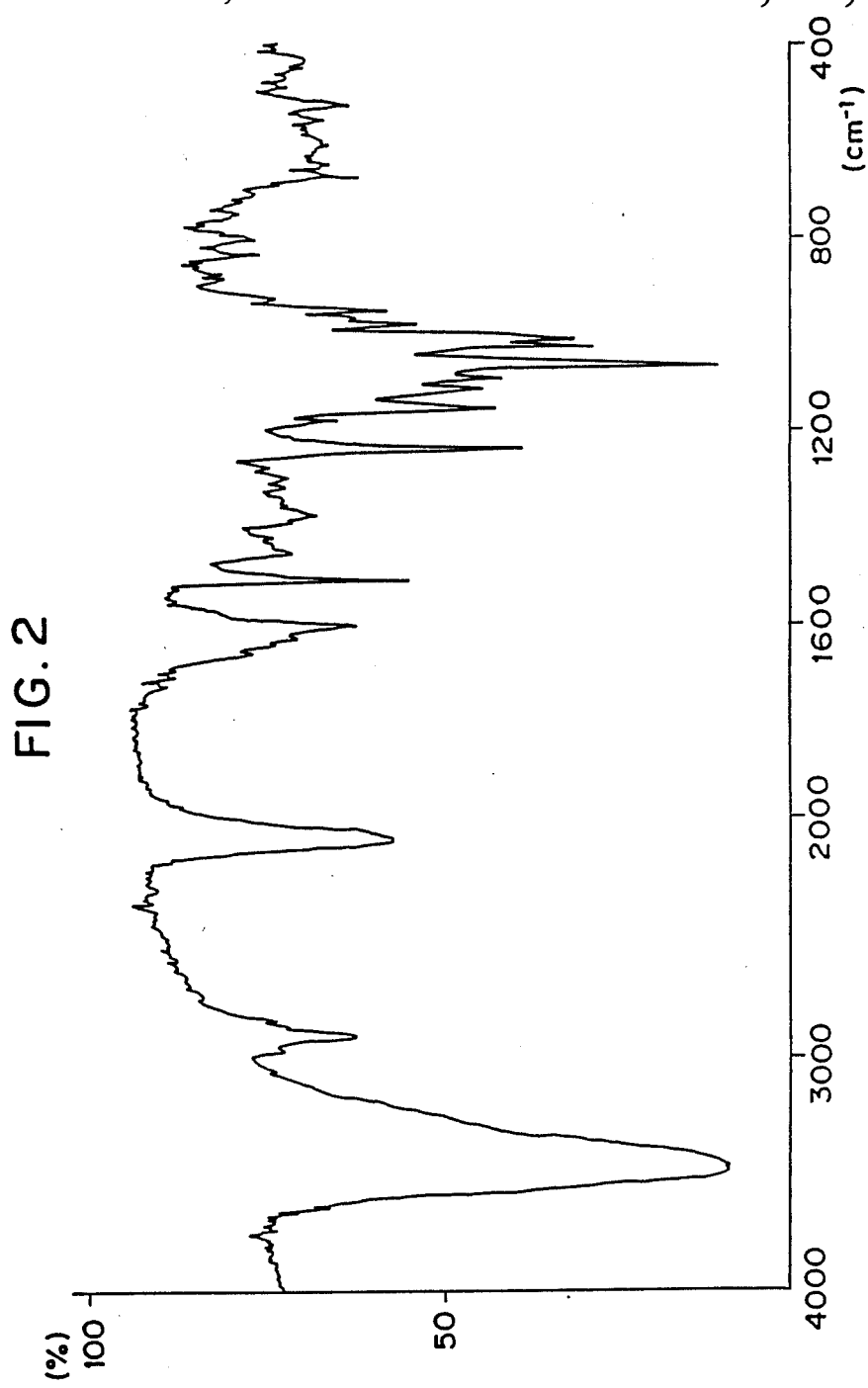
FIGS. 2, 3 and 4 are the infrared spectrum, $^1$H—NMR spectrum, and $^{13}$C—NMR spectrum, respectively, of the same substance.

(d) Infrared absorption spectrum (KBr Method)
see FIG. 2

Figure 3:
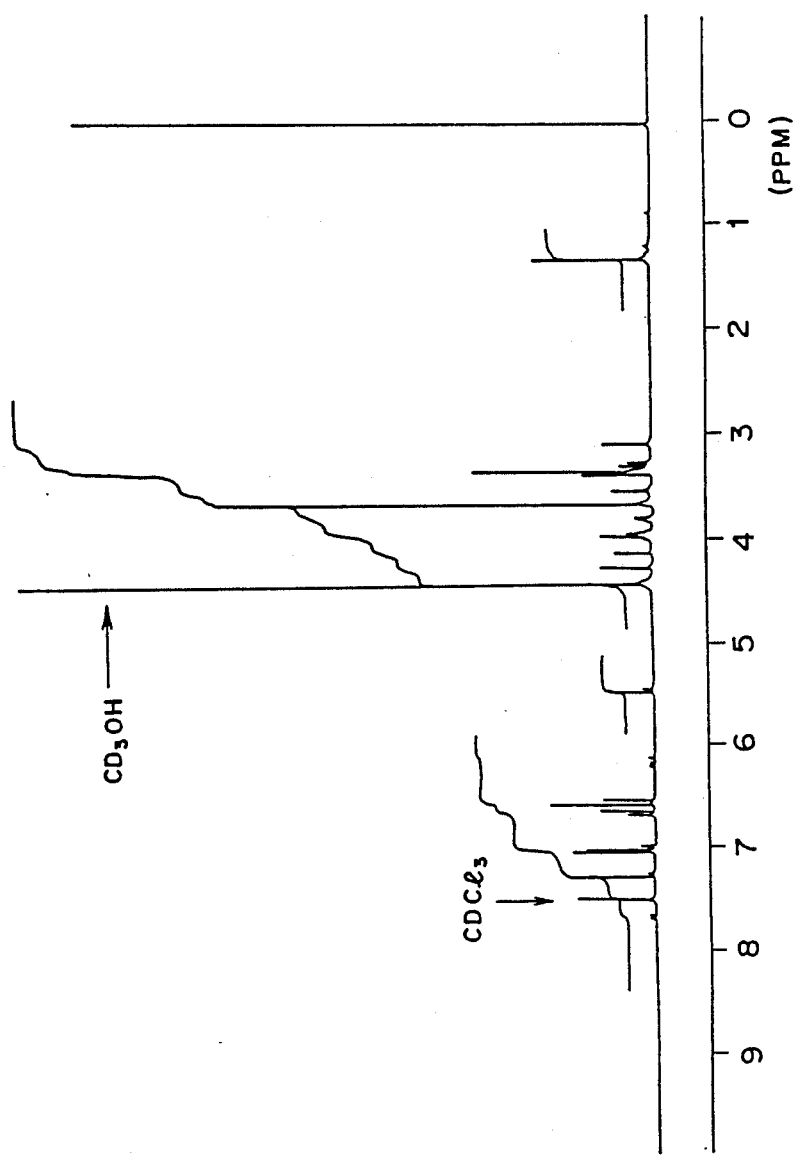

(e) $^1$H—NMR spectrum (CDCl$_3$/CD$_3$OH)
See FIG. 3

Figure 4:
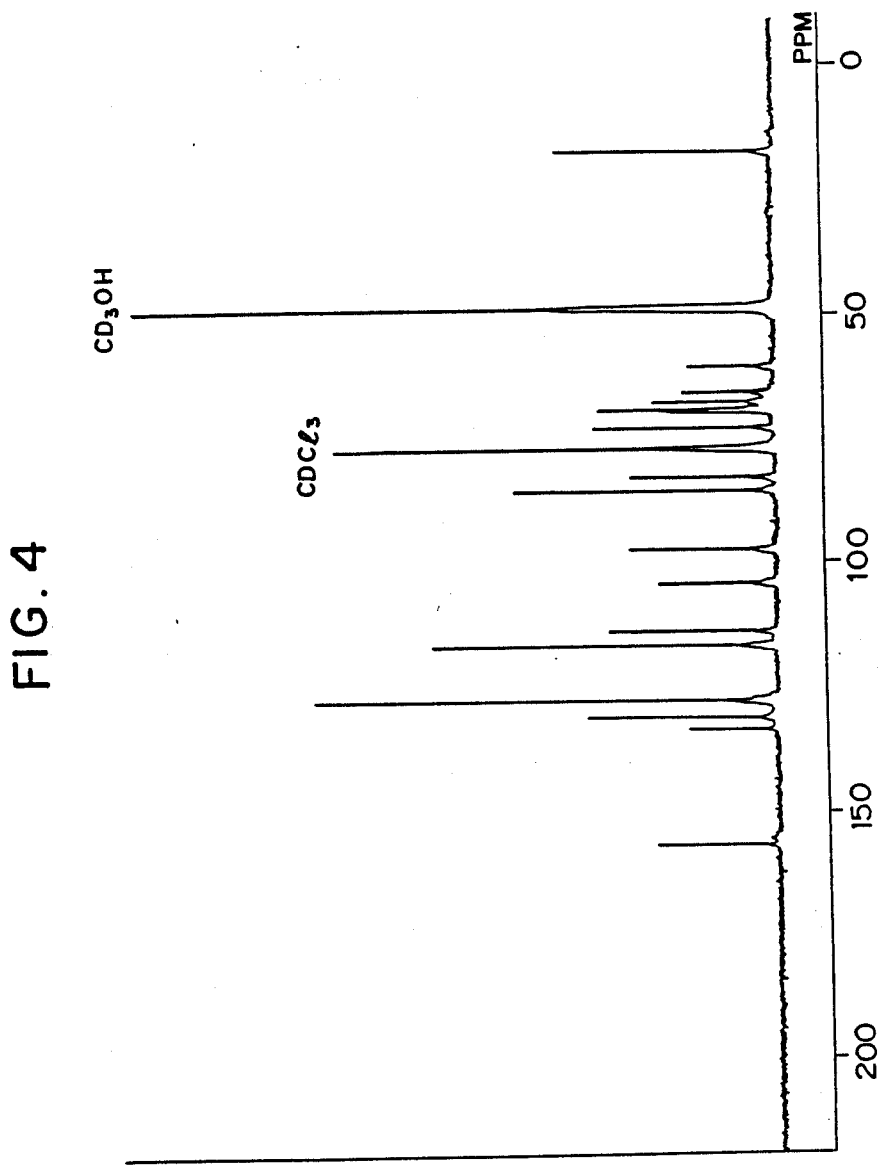

(f) $^{13}$C—NMR spectrum (CDCl$_3$/CD$_3$OH)
See FIG. 4

(g) Solubility to solvents
Soluble in methanol and chloroform and not soluble in n-hexane.

(h) Color and state of the substance
Light yellow crystals (m) Thin layer chromatography
Carrier: Silica gel

| Developing Solvent | | $R_f$ |
|---|---|---|
| Chloroform/methanol | (10:1) | 0.27 |
| Benzene/methanol | (10:4) | 0.57 |

The antibiotic YI-HU3 of this invention has the following biological characteristics:

(a) Activity on plant pathogenic fungus

The activity of the antibiotic YI-HU3 of this invention on plant pathogenic fungus was studied using paper disk plate method. A potato/glucose agar medium was used as the medium for the test, and *Botrycis cinera* and *Collethotricum groeosporioides* were used as test fungus. The results are shown in Table 1.

TABLE 1

| Fungi | Minimum growth inhibition concentration (mg/ml) |
|---|---|
| *Botrycis cinera* | 0.1 |
| *Collethotricum groeosporioides* | 0.1 |

(b) Antitumour Activity S-180 ascites tumor cells were intraperitoneally inoculated into dd-Y mice (1×10$^6$ per mouse). Starting from the next following day and for ten days, 3 μg/day of YI-HU3 was intraperitoneally injected to each mouse to observe survival of the mice. The results are shown in Table 2.

TABLE 2

| | Mouse Survival Rate (%) Passage of Time (days) | | |
|---|---|---|---|
| | 30 | 60 | 120 |
| Group to which YI-HU3 was given | 100 | 100 | 100 |
| Group to which physiological saline was given | 10 | 0 | 0 |

(c) Activity on general microorganisms

Activity of the antibiotic YI-HU3 on the bacteria, fungus, and yeast listed in Table 3 was tested using paper disk plate method. The results are shown in Table 3.

TABLE 3

| Microorganisms | Minimum growth inhibition concentration (mg/ml) |
| --- | --- |
| *Escherichia coli* | 0.01 |
| *Pseudomonas aureofaciens* | 0.01 |
| *Bacillus subtilis* | 0.02 |
| *Aspergillus niger* | 0.05 |
| *Saccharomyces cerevisiae* | 0.03 |

As described above the antibiotic YI-HU3 of this invention has a broad antimicrobial and antitumour activities, and thus is useful as a medicine and an agrochemical.

[EXAMPLE]

The invention is now described by way of an example.

Example

Pseudomonas sp. YI-HU strain (FERM P-9035) was inoculated into a 1,000 ml of liquid medium (pH 6.8) which contains 24 g of potato-dextrose medium (produced by Difco Co.) per liter, and cultured under shaking at 28° C. for 4 days. After termination of culturing, the broth was centrifuged and chloroform was added to the supernatant to effect phase separation. The chloroform layer was condensed and the condensate was subjected to silica gel (Wacohgel C-200) column chromatography, using chloroform as an eluent to obtain active fractions. After condensation and drying of the fractions, the target compound was dissolved into a chloroform-methanol mixed solvent. Through addition of n-hexane to the solution 10 mg of needle-like, light yellow crystals of YI-HU3 was obtained.

This substance exhibited the above-mentioned physicochemical characteristics.

What is claimed is:

1. Antibiotic YI-HU3 having the following physicochemical characteristics:
    (a) Molecular weight
        469
    (b) Melting point
        180°–190° C.
    (c) Ultraviolet absorption spectrum (in chloroform)
    The maximum absorption is found in the neighborhood of 312 nm, with the second largest absorption being in the neighborhood of 300 nm.
    (d) Infrared absorption spectrum (KBr Method)
        FIG. 2
    (e) $^1$H—NMR spectrum (CDCl$_3$/CD$_3$OH)
        FIG. 3
    (f) $^{13}$C—NMR spectrum (CDCl$_3$/CD$_3$OH)
        FIG. 4
    (g) Solubility to solvents
        Soluble in methanol and chloroform, and not soluble in n-hexane.
    (h) Color and state of the substance
        Light yellow crystals.

* * * * *